United States Patent

Ripa et al.

Patent Number: 6,042,810
Date of Patent: *Mar. 28, 2000

[54] PROCESS FOR THE PREPARATION OF MACROCYCLIC CHELANTS AND THE CHELATES THEREOF WITH PARAMAGNETIC METAL IONS

[75] Inventors: Giorgio Ripa; Alessandro Scala; Marcella Murru; Carlo Felice Viscardi; Marina Ausonio; Chiara Scotti; Patrizia Cossutta, all of Milan, Italy

[73] Assignee: Dibra S.p.A., Italy

[*] Notice: This patent is subject to a terminal disclaimer.

[21] Appl. No.: 09/317,271

[22] Filed: May 24, 1999

Related U.S. Application Data

[62] Division of application No. 09/095,015, Jun. 10, 1998, Pat. No. 5,925,752.

[30] Foreign Application Priority Data

Jun. 11, 1998 [IT] Italy ................. MI97A1371

[51] Int. Cl.[7] .......................... A61B 5/055; C07D 487/22
[52] U.S. Cl. ................. 424/9.363; 540/465; 540/474
[58] Field of Search ............ 424/9.363; 540/465, 540/474

[56] References Cited

U.S. PATENT DOCUMENTS

| | | | |
|---|---|---|---|
| 4,085,106 | 4/1978 | Atkins | 260/256.4 F |
| 5,277,895 | 1/1994 | Platzek et al. | 424/9 |
| 5,447,635 | 9/1995 | Viscardi et al. | 210/636 |
| 5,747,000 | 5/1998 | Platzek et al. | 424/9.363 |
| 5,925,752 | 7/1999 | Ripa et al. | 540/474 |

FOREIGN PATENT DOCUMENTS 4218744 of 1992 Germany .

OTHER PUBLICATIONS

Dischino et al Inorg. Chem. 1991, 30, pp 1265–9 Synthesis of Gadolinium (+)-10-(1-Hydroxypropan-2-yl)-1,4,7,10-tetraazacyclododecane-1,4,7-triyltriacetate etc.

Weisman et al Tetrahedron Letters vol. 21, 1980 pp 3635–8.

*Primary Examiner*—Mukund J. Shah
*Assistant Examiner*—Pavanaram K Sripada
*Attorney, Agent, or Firm*—Nixon & Vanderhye

[57] ABSTRACT

A process for the preparation of complexes of macrocyclic chelants with paramagnetic metal trivalent ions of formula (XII)

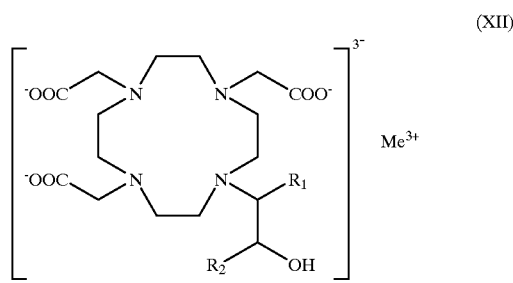

wherein $R_1$, $R_2$ and $Me^{3+}$ are as described in the following, comprising: a) reaction of 1,4,7,10-tetraazacyclododecane with triethyl orthoformate to give 5H,9bH-2a,4a,7,9a-octahydrotetraazacycloocta[cd]pentalene; b) carboxymethylation reaction in water; c) hydrolysis reaction in basic conditions; d) alkylation according to known methods with an epoxide in water; e) complexation according to known methods carried out in water by addition of a paramagnetic metal salt; f) purification by diafiltration, final desalting of the aqueous solution on ion exchange resins and g) crystallization or recovery.

16 Claims, No Drawings

PROCESS FOR THE PREPARATION OF MACROCYCLIC CHELANTS AND THE CHELATES THEREOF WITH PARAMAGNETIC METAL IONS

This is a Divsion of application Ser. No. 09/095,015, filed Jun. 10, 1998, now U.S. Pat. No. 5,925,752.

The present invention relates to a process for the preparation of macrocyclic chelates with paramagnetic metal ions of formula (XII)

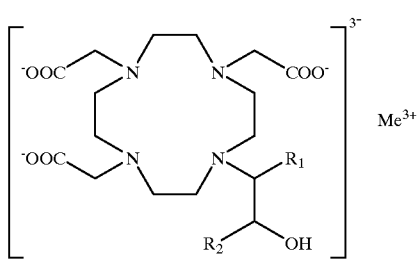

wherein
R$_1$ and R$_2$ are independently a hydrogen atom, a (C$_1$–C$_{20}$) alkyl containing 1 to 10 oxygen atoms, or a phenyl, phenyloxy, phenyldioxy group, which can be unsubstituted or substituted with a (C$_1$–C$_5$) alkyl or hydroxy, (C$_1$–C$_5$) alkoxy, carbamoyl or carboxylic groups;
Me$^{3+}$ is the trivalent ion of a paramagnetic metal.

This type of complexes with metal ions, in particular with paramagnetic metal ions, is used for the preparation of non-ionic contrast agents for the diagnostic technique known as magnetic resonance (MRI, Magnetic Resonance Imaging), among which are ProHance(R) (Gadoteridol, gadolinium complex of 10-(2-hydroxy-propyl)-1,4,7,10-tetraazacyclododecane-1,4,7-triacetic acid), and Gadobutrol (gadolinium complex of [10-[2,3-dihydroxy-1-(hydroxymethyl)propyl]-1,4,7,10-tetraazacy-clododecane-1,4,7-triacetic acid).

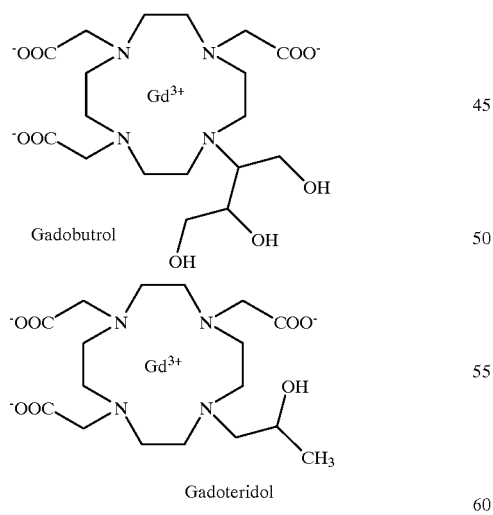

Two different synthetic approaches are described in literature for the preparation of this kind of complexes, the approaches differing in the strategy taken to discriminate one of the four nitrogen atoms: the first one (Dischino et al., Inorg. Chem., 1991, 30, 1265 or EP 448191, EP 292689, EP 255471) is based on the selective protection of one of the nitrogen atoms by formation of the compound of formula (III), 5H,9bH-2a,4a,7-tetraazacycloocta[cd]pentalene, and on the subsequent hydrolysis to the compound of formula (IV), 1-formyl-1,4,7,10-tetraazacyclododecane, followed by the carboxymethylation of the still free nitrogen atoms and by the deprotection and alkylation of the fourth nitrogen atom, according to scheme 1.

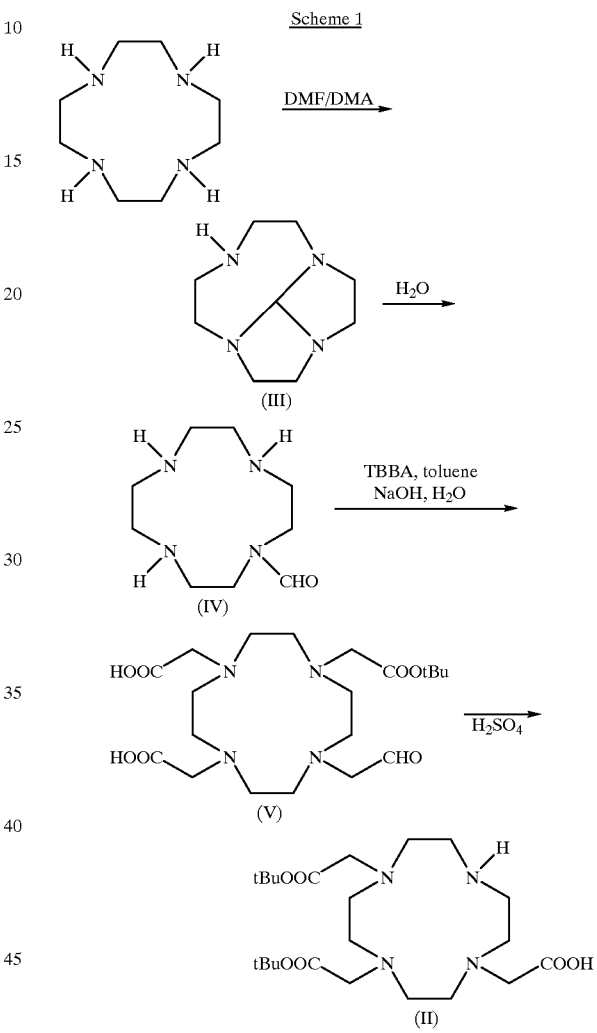

The step from 1,4,7,10-tetraazacyclododecane disulfate (a commercially available product) to compound (III) is effected according to the conventional method disclosed in U.S. Pat. No. 4,085,106, followed by formation of the compound of formula (IV) in water-alcohol medium.

This intermediate is subsequently tricarboxymethylated with tert-butyl bromoacetate (TBBA) in dimethylformamide at 2.5° C. and then treated with a toluene-sodium hydroxide diphasic mixture to give the compound of formula (V), 10-formyl-1,4,7,10-tetraazacyclododecane-1,4,7-triacetic, tris(1,1-dimethylethyl) ester, which is subsequently hydrolysed to compound of formula (II) in acidic solution.

In the process described in WO 93/24469 for the synthesis of Gadobutrol, at first one of the nitrogen atoms is alkylated in conditions such as to minimize the formation of polyalkylated derivatives, then the monoalkylderivative is purified and carboxymethylated, according to scheme 2.

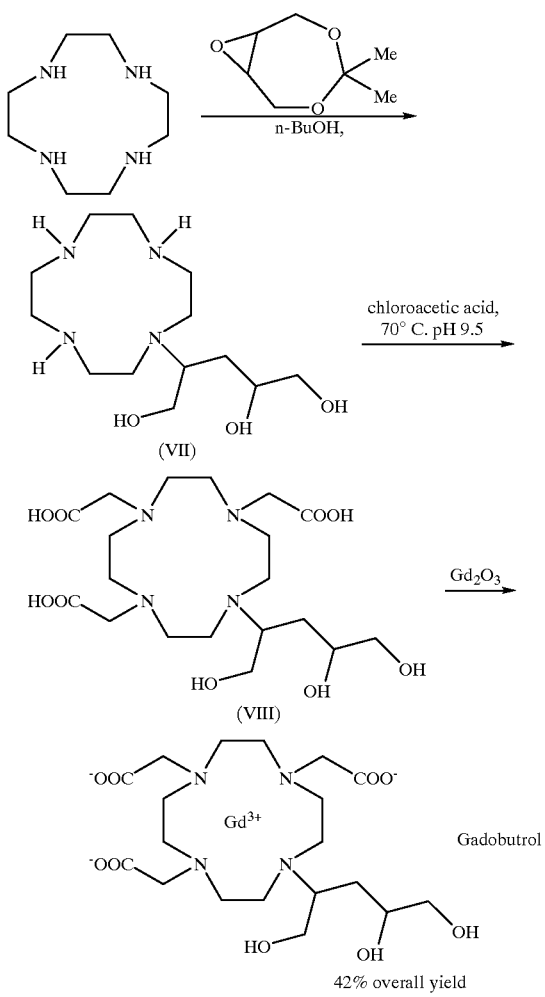

Scheme 2

The alkylation of 1,4,7,10-tetraazacyclododecane with the epoxide of formula (VI), 4,4-dimethyl-3,5,8-trioxabicyclo[5.1.0]octane, is carried out in anhydrous n-BuOH under reflux and the reaction mixture is extracted with water, evaporated to dryness and the residue is subsequently diluted with water and extracted with methylene chloride.

The aqueous phase containing the mono-alkylated product (65% yield in Example 7 which reports the procedure for the preparation of 5 kg of Gadobutrol) is directly carboxymethylated at 70° C. with chloroacetic acid, keeping pH 9.5 by addition of NaCH. The reaction mixture is adjusted to pH 1, concentrated to dryness and dissolved in methanol to remove the undissolved salts. The filtrate is then concentrated under vacuum, dissolved in water, and loaded onto a cation exchanger in the H⁺ form to fix the product. The subsequent elution with ammonia displaces the desired product, which is concentrated to small volume and subsequently complexed with gadolinium oxide according to conventional methods, and the resulting complex is purified by means of ion exchange resins. The overall yield is 42%.

Although the first of these two processes could theoretically provide a higher yield, in that all the individual steps (protection, carboxymethylation and deprotection) are highly selective, the complexity of the operations required to remove salts and solvents and to purify the reaction intermediates makes such theoretical advantage ineffective: the overall yield is in fact, in the case of Gadoteridol, slightly higher than 37%.

The preparation of Gadobutrol according to the alternative process (WO 93/24469) provides a markedly better yield (72%) only on a laboratory scale (example 2): example 7 (represented in the above Scheme 2) actually evidences that, when scaling-up, the yield of this process also remarkably decreases (42%).

In addition to the drawback of an about 40% yield, both processes of the prior art are characterized by troublesome operations, which often involve the handling of solids, the use of remarkable amounts of a number of different solvents, some of them having undesirable toxicological or at least hazardous characteristics.

Moreover, the synthesis described by Dischino makes use of reagents which are extremely toxic, such as tertbutyl bromoacetate, or harmful and dangerous from the reactivity point of view, such as dimethylformamide dimethylacetal.

It is the object of the present invention to provide a process for the preparation of the complexes of general formula (XII)

wherein $R_1$ and $R_2$ are independently a hydrogen atom, a $(C_1-C_{20})$ alkyl containing 1 to 10 oxygen atoms, or a phenyl, phenyloxy, phenyldioxy group, which can be unsubstituted or substituted with a $(C_1-C_5)$ alkyl or hydroxy, $(C_1-C_5)$ alkoxy, carbamoyl or carboxylic groups, $Me^{3+}$ is the trivalent ion of a paramagnetic metal;

comprising the steps represented in the following Scheme 3:

Scheme 3

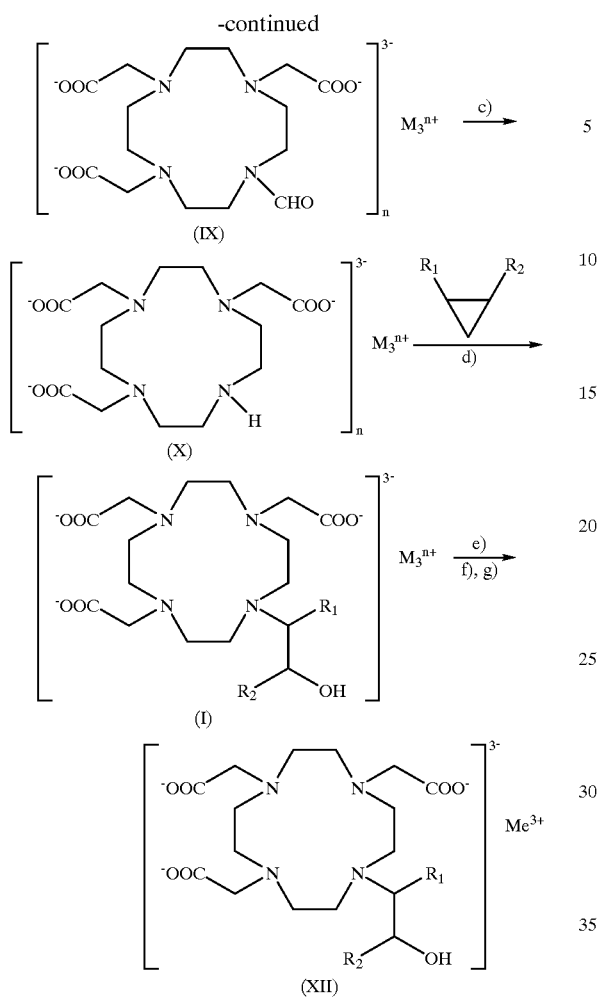

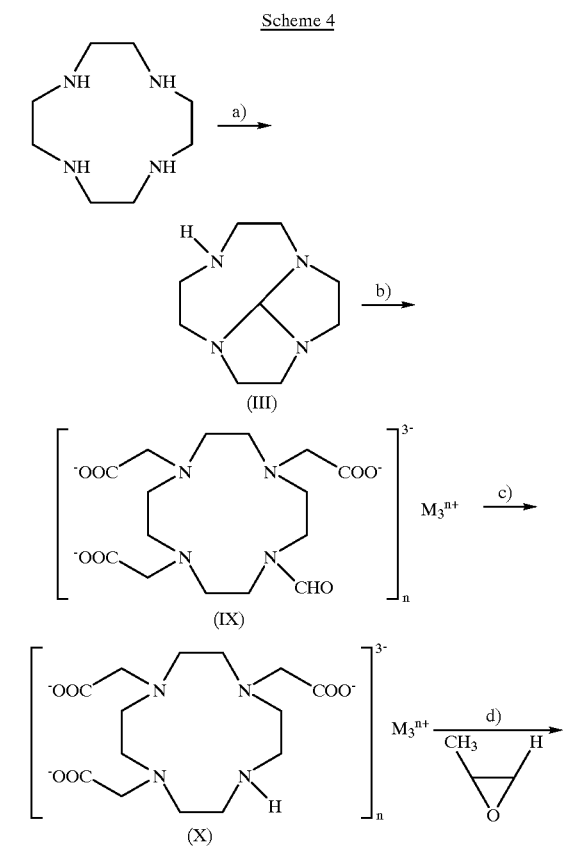

wherein:
 a) is the formation of 5H,9bH-2a,4a,7,9a-octahydro-tetraazacycloocta[cd]pentalene of formula (III) starting from 1,4,7,10-tetraazacyclododecane with triethyl orthoformate, in the presence of an acid catalyst;
 b) is the carboxymethylation reaction of compound (III), in water, in molar ratios ranging from 3 to 5 mol/ mol of haloacetic acid to compound (III), at pH ranging from 9.5 to 12.5 by addition of an alkali or alkaline-earth metal hydroxide, at a temperature between 7 and 50° C., for a time from 3 to 48 h, to give the intermediate salt of 10-formyl-1,4,7,10-tetraazacyclododecane-1,4,7-triacetic acid of formula (IX) which is hydrolized in step c), without being isolated;
 c) is the hydrolysis reaction of intermediate (IX), in water, in basic conditions by addition of the same base as in step b), at pH higher than 12.5, at a temperature from 65° C. to 100° C. and for a time from 5 to 48 h, to give an aqueous solution of the 1,4,7,10-tetraazacyclododecane-1,4,7-triacetic acid salt of formula (X), which undergoes step d) without being isolated;
 d) is the alkylation reaction, according to known methods, carried out in water with an epoxide of formula (XI), in which $R_1$ and $R_2$ have the meanings defined above, to give compound (I) as a salt, which undergoes step e) without being isolated;
 e) is a complexation step, according to known methods, effected in water by addition of a salt of the paramagnetic metal trivalent ions having atomic numbers variable from 20 to 31, 39, 42, 43, 44, 49, or from 57 to 83, to give the aqueous solution of the paramagnetic complex of formula (XII), which undergoes step f) without being isolated;
 f) is a purification step, consisting of: diafiltration of the aqueous solution of compound (XII) to remove most salts and low-molecular weight impurities, optionally preceded by a chromatographic purification step to remove the lipophilic impurities; final desalting of the aqueous solution on ion exchange resins; and
 g) crystallization or recovery of compound (XII).

The process of the present invention keeps the high selectivity typical of the protection/deprotection strategy described by Dischino in the above mentioned paper, while removing all its drawbacks, thus providing for the first time a reproducible industrial process for the preparation of the concerned compounds in high yields and without use of hazardous substances.

The preparation of the gadolinium complex of 10-(2-hydroxypropyl)-1,4,7,10-tetraazacyclododecane-1,4,7-triacetic) acid (Gadoteridol), according to scheme 4, is particularly preferred:

Scheme 4

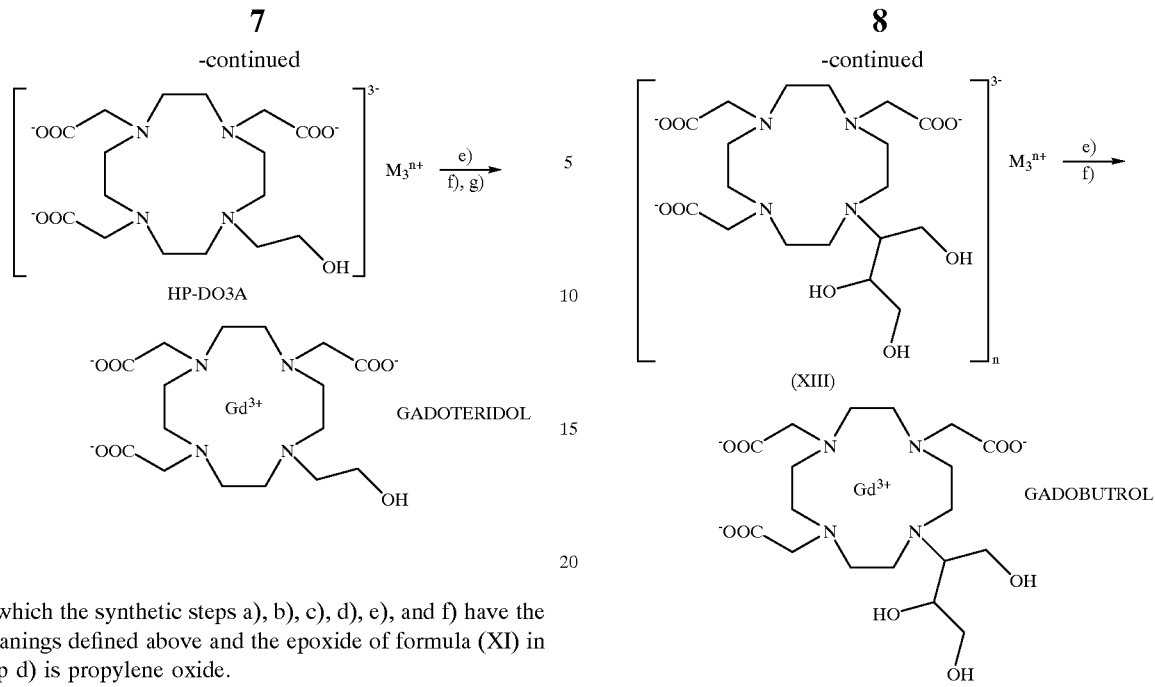

in which the synthetic steps a), b), c), d), e), and f) have the meanings defined above and the epoxide of formula (XI) in step d) is propylene oxide.

The preparation of the gadolinium complex of [10-[2,3-dihydroxy-1-(hydroxymethyl)propyl]-1,4,7,10-tetraazacyclododecane-1,4,7-triacetic) acid (Gadobutrol), according to the scheme 5, is also preferred.

Scheme 5

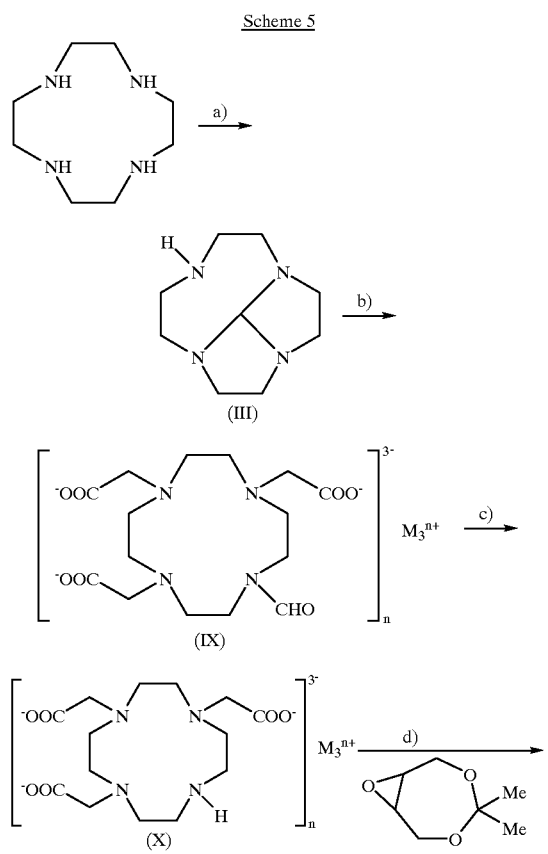

in which the synthetic steps a), b), c), d), e), and f) have the meanings defined above and the epoxide of formula (XI) in step d) corresponds to the one of formula (VI), defined above.

On the other hand, step a) of the process of the present invention involves the use of triethyl orthoformate in the presence of an acid catalyst, instead of dialkylformamide-dialkylacetal.

Triethyl orthoformate can be added in amounts ranging from 105% to 200% on the stoichiometric value.

The reaction temperature can range from 110 to 150° C. and the reaction time from 5 to 24 h.

The catalyst is a carboxylic acid having at least 3 carbon atoms, $C_3$–$C_{18}$, preferably selected from the group consisting of propionic, butyric and pivalic acids.

Triethyl orthoformate is a less toxic and less expensive product than N,N-dimethylformamide-dimethylacetal and does not involve the formation of harmful, not-condensable gaseous by-products. Moreover, triethyl orthoformate is less reactive than the N,N-dimethylformamide-dimethylacetal reagent, which makes it possible to carry out the loading procedures of the reagent as well as the reaction itself under totally safe conditions even on a large scale, allows one to better monitor the progress of the reaction on the basis of such operative parameters as time and temperature, without checking the progress by gas chromatography, and makes dosing the reactive less critical, in that it can be added from the very beginning without causing the formation of undesired by-products: all that rendering the process suitable for the production of compound (III) on the industrial scale in easily reproducible conditions.

The subsequent step b) involves the carboxymethylation of compound (III) in aqueous solution, using a haloacetic acid, to give compound (IX), i.e. the 10-formyl-1,4,7,10-tetraazacyclododecane-1,4,7-triacetic acid salt with an alkali or alkaline-earth metal, the salts of compound (IX) with sodium, potassium or calcium being most preferred.

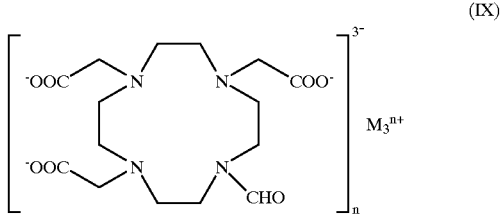

(IX)

The preferred conditions to carry out step b) are the following ones:

haloacetic acid to compound (III) molar ratio from 3.2 to 4.5;
pH from 10 to 12;
the haloacetic acid is chloroacetic or bromoacetic, preferably bromoacetic, acid.

Step c) is the hydrolysis reaction of intermediate (IX) in water, in basic conditions by addition of the same base as in step b), at pH higher than 12.5, at a temperature from 65° C. to 100° C. and for a time from 5 to 48 h, to give an aqueous solution of the salt of compound (X), which undergoes step d) without being isolated.

The process of the present invention thus makes it possible to carry out the carboxymethylation of compound (III) and the hydrolysis of compound (IX) in aqueous solution, thereby completely avoiding the use of undesired organic solvents.

Step d) is the alkylation reaction of compound (X) according to methods described in literature.

For example, in the case of the preparation of Gadoteridol, as described in EP 292,689, the alkaline aqueous solution of the compound (X) is treated with propylene oxide at room temperature to give, after the alkylation reaction, 10-(2-hydroxypropyl)-1,4,7,10-tetraazacyclododecane-1,4,7-triacetic acid (commonly known as HPDO3A).

The case of Gadobutrol is quite the same, except for the use of 4,4-dimethyl-3,5,8-trioxabicyclo-[5.1.0]octane of formula (VI) as alkylating agent in place of propylene oxide.

Step e) is the complexation reaction, according to conventional methods, carried out in water by addition of a salt of the paramagnetic metal trivalent ions having atomic number variable from 20 to 31, 39, 42, 43, 44, 49, or from 57 to 83.

The trivalent ions of Gd, Dy, Yb metals are preferred, gadolinium being most preferred.

Step f) is a purification step, consisting of: diafiltration of the aqueous solution to remove most salts and low-molecular weight impurities, optionally preceded by a chromatographic purification step to remove the lipophilic impurities; a final desalting of the aqueous solution on ion exchange resins; and crystallization and recovery.

The diafiltration treatment is useful to remove most salts, which are present in the solution from the preceding steps in remarkable amounts as by-products from the carboxymethylation and hydrolysis reactions.

Diafiltration can be carried out using commercial nanofiltration membranes, characterized by very high permeability to monovalent ions but substantially impermeable to the gadolinium complexes of general formula (I): for example, the spiral-wound membrane elements Desal DK, Dow Chemical Filmtec NF45 and Daicel DRA can be cited.

Diafiltration can be carried out according to the teachings by Bungay P. M. et al., ("Synthetic Membranes", Science Engineering Application, D. Reidel, C181, 1986) or also in the conditions described in U.S. Pat. No. 5,447,635.

The crude solution can be fed to nanofiltration through a in line filter, for example a cartridge, to remove any gadolinium oxide particles present, and possibly also through a column containing an absorbing resin or a reversed-phase liquid chromatography stationary phase, in order to remove chromatographically the more lipophilic impurities.

In this case, the product can be eluted with water from the resin, and the aqueous eluate can be combined with the product fraction and reconcentrated in the same nanofiltration unit.

The absorbing resin can be selected from those commercially available: for example, R&H XAD1600 or 1600T, Bayer Lewatit OC1062 or 1064, Diaion SP800 or SP825 can be cited.

The treated solution is, as a result, concentrated and free from most salts, but it still contains small amounts of inorganic salts and significant amounts of organic ionic impurities, therefore it is fed to a ion exchange unit for the final purification from ionic impurities.

The ion exchange unit should preferably be designed so that the product is not subjected to pH values below 4, which would cause a significant loss of yield due to the dissociation of the gadolinium complex: after dissociation into free ligand and gadolinium, both ligand and gadolinium would be blocked by the resin.

To avoid this drawback, desalting cannot be carried out in separate bed units containing strongly acidic ion exchangers: it can be carried out, on the contrary, in a mixed bed unit or, better, in a separate bed unit which uses no strongly acidic cation exchangers: for this purpose, a unit consisting of 4 beds can be used, the first bed (C1) being a strongly basic anion exchanger in the hydrogen carbonate form, the second (C2) being a weakly acidic cation exchanger in the $H^+$ form, the third (C3) being a small size, strongly basic anion exchanger in the $OH^-$ form and the fourth (C4) being a small size, weakly acidic cation exchanger in the $H^+$ form.

The strongly basic anion exchanger can be selected from a group consisting of any of the commercially available, gel or macroporous, type I or type II exchanges resins, for example R&H Amberjet 4200 or 4400 or IRA 900, Diaion Relite 3A or 3AS, Dow Chemical Dowex Monosphere AI500 or AI550 or AII500.

When available, commercial grades are preferred, which are characterized by particles conventionally defined as in small size, since they provide a faster exchange: for example, in the case of the Diaion 3A or 3AS resins, the "fb" grade is preferred, and for the Dowex Monosphere AI resin the AI500 grade is preferred.

The weakly acidic cation exchanger can be selected from a group consisting of all the commercially available products: the gel-matrix products are preferred to the macroporous-matrix ones. For example, among the preferred resins, R&H IRC86, Diaion Relite CC and Dow Chemical Dowex CCR3 can be cited.

When available, commercial grades characterized by particles conventionally defined as small size are preferred, since they provide a faster exchange: for example, in the case of the Dow Chemical Dowex CCR3 resin, the "lb" grade is preferred.

The desalted solution, which usually contains only the desired product at very high purity, can then be concentrated by heating to a dry residue or to a viscous residue and then added with a solvent, typically a water-soluble alcohol, to precipitate the final product.

In the case of the preparation of Gadoteridol and Gadobutrol according to the process of the present invention, a high quality final product can be obtained in yield equal to or higher than 80%. No traces of impurities can be detected in the final products.

The following examples illustrate the best experimental conditions to carry out the process of the invention.

EXPERIMENTAL SECTION

EXAMPLE 1

Preparation of Gadoteridol

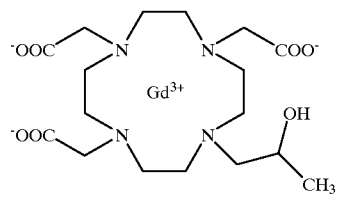

A) Preparation of 5H,9bH,2a,4a,7-octahydrotetraazacyclododecaner[cd]pentalene 23.8 kg (0.138 kmol) di 1,4,7,10-tetraazacyclododecane, containing 0.7% w/w of water, are dissolved in 23.8 kg of amyl alcohol. The water-amyl alcohol azeotrope and the amyl alcohol excess are distilled in succession under reduced pressure, then 24.5 kg (0.166 kmol) of triethyl orthoformate and 355 g of propionic acid are added, under nitrogen atmosphere. The mixture is heated for 11 h at 125° C., while distilling the formed ethanol, then the reaction mass is cooled to 35° C., to obtain the desired compound as a fluid oil.

B) Preparation of 10-formyl-1,4,7,10-tetraazacyclodo-decane-1,4,7-triacetic acid sodium salt The compound from A) is added to a solution prepared dissolving 81.5 kg (0.469 kmol) of bromoacetic acid and about 62.6 kg of 30% w/w NaOH in 100 kg of water to pH 5. During the addition of the crude compound, pH is kept at 11 by addition of NaOH; at the end of the addition pH is increased to 11.1 again by addition of 30% w/w NaOH, and the mixture is reacted for 24 h at 35° C. at the same pH value.

C) Preparation of 1,4,7,10-tetraazacyclododecane-1,4,7-triacetic acid sodium salt (DO3A)

77.3 kg of 30% w/w NaOH are added to compound from step b), heating at 70° C. for 9 h. The resulting aqueous solution contains 0.131 kmol of the desired compound (content determined by HPLC), as the trisodium salt.

D) Synthesis of Gadoteridol pH is adjusted to 12.3 with conc. HCl, 15.2 kg (0.262 kmol) of propylene oxide are added and the mixture is reacted for 4 h at 40° C. After that, the solution is heated to 50° C. and 120 kg of an aqueous solution containing 0.135 kmol of gadolinium trichloride are added. After 1 h, the reaction is cooled to 17° C. and acidified to pH 1.7 with conc. HCl, keeping this pH for 2 h. Subsequently, the solution is heated to 50° C. and pH is adjusted to 7 with sodium hydroxide, keeping these conditions for 1 h.

E) Prepurification of the Gadoteridol crude solution

The Gadoteridol crude solution from the previous step is cooled and transferred to a nanofiltration unit fitted with Desal DK4040F components through a in line filter and a column packed with 150 L of R&H Amberlite XAD 1600 resin. When the reactor is empty, the reactor, the in line filter and the column are washed three times with 300 L of deionized water.

The resulting washing solution is combined with the product solution in the nanofiltration unit, where the product is concentrated and partially desalted under 32 bar and at 25° C.

250 L of crude Gadoteridol solution with a conductivity of 2.9 mS/cm are obtained finally.

F) Final desalting

The Gadoteridol solution is then fed at 200 L/h to a series of 4 ion exchanger beds, the first (C1) consisting of 120 L of strongly basic anion exchanger Relite 3ASfb in the hydrogen carbonate form, the second (C2) consisting of 100 L of weakly acidic cation exchanger Relite CC in the $H^+$ form, the third (C3) consisting of 20 L of Relite 3ASfb in the $OH^-$ form and the fourth (C4) consisting of 20 L of Relite CC resin in the $H^+$ form. All the columns are vented to the atmosphere and the liquid from the second column is passed through a gas separation tank, connected with a vacuum pump, to remove the evolved $CO_2$ from the solution. The outlet from the fourth column is fitted with a density transmitter to detect the product in the eluate.

The first 180 L of eluate are discarded; the eluate is then collected in a product-rich fraction. When all the crude Gadoteridol solution has been loaded onto the ion exchange unit, the product is eluted with 600 L of deionized water, the eluate is then combined with the product-rich fraction, which is colourless and substantially free from salt impurities (conductivity 2.2 $\mu S/cm$).

The yield of the final desalting, determined on the basis of the HPLC assay, is 98%.

G) Recovery of the product (Gadoteridol)

The product-rich fraction is then thermally concentrated to a thick residue, which is added with 350 kg of isopropanol at 79° C. The resulting suspension is refluxed for 1 h, then cooled, centrifuged and dried under reduced pressure, to obtain 68.2 kg of Gadoteridol containing 10% of hydration water (0.111 kmol), HPLC assay 98.5% (s.a.).

Overall yield: 80.7%

The IR and MS spectra are consistent with the indicated structure.

EXAMPLE 2

Preparation of Gadobutrol

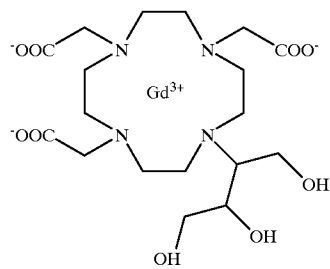

The procedure of Example 1 is followed until step C included, to obtain a solution of DO3A trisodium salt.

pH is adjusted to 12.3 with conc. HCl and 57.7 kg (0.4 kmol) of 4,4-dimethyl-3,5,8-trioxabicyclo[5.1.0]-octane are added. After reaction for 4 h at 40° C. and for 8 h at 80° C., the solution is cooled to 50° C., 120 kg of an aqueous solution containing 0.135 kmol of gadolinium trichloride are added. After 1 h the mixture is cooled at 17° C. and acidified to pH 1.7 with conc. HCl, keeping this pH for 2 h. The solution is subsequently warmed to 50° C., pH is adjusted to 7 with sodium hydroxide, keeping these conditions for 1 h.

After that, the resulting crude Gadobutrol is purified repeating exactly the same process as in steps E and F of Example 1.

Recovery of the product (Gadobutrol)

The product-rich fraction is then thermally concentrated to a viscous residue and the residue is added with 350 kg of ethanol at 79° C.

The resulting suspension is refluxed for 1 h, then cooled, centrifuged and dried under reduced pressure to obtain 66.0 kg of Gadobutrol (0.109 kmol), HPLC assay 99.5% (A%).

Overall yield: 79.1%

The IR and MS spectra are consistent with the indicated structure.

We claim:

1. A process for the preparation of complexes of 10-[2,3-dihydroxy-1-(hydroxymethyl)propyl]- 1,4,7,10-tetraazacyclododecane- 1,4,7-triacetic acid with trivalent ions of paramagnetic metals of formula (XII)

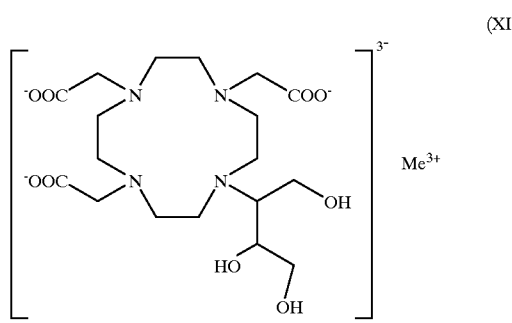

wherein $Me^{3+}$ is the trivalent ion of a paramagnetic metal, said process comprising the steps shown in the following scheme:

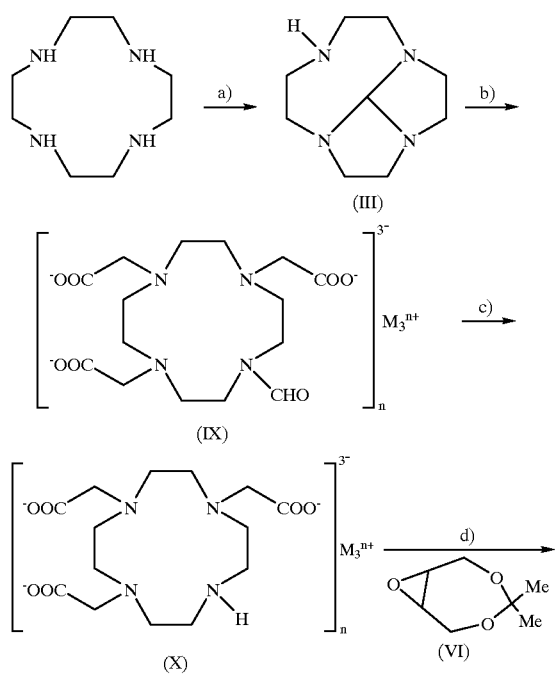

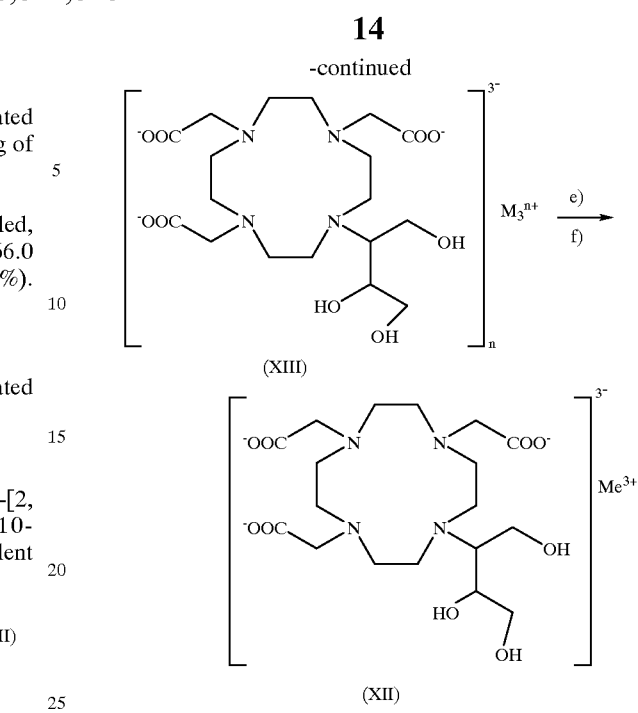

a) reaction of 1,4,7,10-tetraazacyclododecane with triethyl orthoformate in the absence of solvent and in the presence of an acid catalyst, at an elevated temperature, to give 5H, 9bH-2a, 4a, 7, 9a-octahydrotetraazacycloocta[cd]pentalene of formula (III):
b) carboxymethylating compound (III) in water, under basic conditions, with a haloacetic acid, to give the intermediate of formula (IX), which is subjected to the hydrolysis reaction of the subsequent step c) without being isolated;
c) hydrolyzing intermediate (IX) in basic conditions, by adding the same base as added in step b), to give an aqueous solution of the salt of formula (X), which undergoes the subsequent step d), without being isolated,
d) alkylating in water, with propylene epoxide to give a corresponding salt of 10-(2-hydroxypropyl)- 1,4,7,10-tetracyclododecane- 1,4,7-triacetic acetic which undergoes step e) without being isolated;
e) complexing in water by adding a salt of a paramagnetic metal having atomic number ranging from 20 to 31, 42, 43, 44, 49 and from 50 to 57;
f) purifying by diafiltration the aqueous solution of compound (XII) to remove most salts and low-molecular weight impurities, optionally preceded by chromatographic purification to remove the lipophilic impurities; final desalting of the aqueous solution on ion exchange resins, and crystallizing or recovering of compound (XII).

2. A process as claimed in claim 1, in which, in step a), triethyl orthoformate is used in amounts ranging from 105 to 200% of the stoichiometry.

3. A process according to any one of claims 1–2, in which, in step a), the reaction temperature ranges from 110 to 150° C. and the reaction time ranges from 5 to 24 hours.

4. A process according to any one of claims 1–3, in which, in step a), the acid catalyst is a carboxylic acid having at least 3 carbon atoms.

5. A process according to any one of claims 1–4, in which, in step b), the salt of compound (IX) is selected from sodium, potassium and calcium.

6. A process according to any one of claims 1–5, wherein the carboxymethylation reaction of step b) is carried out between compound (III) and haloacetic acid, in molar ratios of 3 to 5 mol/ mol of haloacetic acid to compound (III), at pH from 9.5 to 12.5 by addition of an alkali or alkaline-earth metal hydroxide, at a temperature between 7 and 50° C., for a time from 3 to 48 hours.

7. A process as claimed in claim 6, in which, in step b), the haloacetic acid to compound (III) molar ratio ranges from 3.2 to 4.5 and pH is from 10 to 12.

8. A process according to any one of claims 1–7, in which, in step c), the reaction is carried out at pH higher than 12.5, at a temperature from 6 to 100° C., for a time from 5 to 48 hours.

9. A process according to any one of claims 1–8, wherein the haloacetic acid in step b) is bromoacetic acid.

10. A process according to any one of claims 1–9, wherein the paramagnetic metal is selected from: Gd, Dy, Yb.

11. A process according to any one of claims 1–10, wherein, in step f), a 4 bed unit is used, the first bed consisting of a strongly basic anion exchanger in the hydrogen carbonate form, the second consisting of a weakly acidic cation exchanger in the $H^+$ form, the third consisting of a strongly basic anion exchanger in the $OH^-$ form and the fourth consisting of a weakly acidic cation exchanger in the $H^+$ form.

12. A process according to any one of claims 1–11, wherein, in step f), resins with small size particles are used.

13. A process according to any one of claims 1–12, wherein, in step f), the strongly basic ion exchanger is selected from the group consisting of gel- or macroporous-matrix resins of type I or of type II.

14. A process according to any one of claims 1–12, wherein, in step f), the weakly acidic ion exchanger is selected from group consisting of gel-matrix resins.

15. A process according to any one of claims 1–14, wherein step f) comprises a chromatographic purification to remove the lipophilic impurities before the diafiltration step.

16. A process according to any one of claims 1–15, wherein, in formula (XII), $R_1$ is methyl, $R_2$ is hydrogen, $Me^{3+}$ is $Gd^{3+}$ and the epoxide of formula (XI) is propylene oxide.

* * * * *